United States Patent
Bond et al.

(10) Patent No.: US 7,647,089 B2
(45) Date of Patent: Jan. 12, 2010

(54) SURFACE IDENTIFICATION USING MICROWAVE SIGNALS FOR MICROWAVE-BASED DETECTION OF CANCER

(75) Inventors: Essex Julian Bond, Madison, WI (US); Susan Carol Hagness, Madison, WI (US); Barry Dean Van Veen, McFarland, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 620 days.

(21) Appl. No.: 11/340,214

(22) Filed: Jan. 26, 2006

(65) Prior Publication Data

US 2006/0183995 A1 Aug. 17, 2006

Related U.S. Application Data

(60) Provisional application No. 60/648,295, filed on Jan. 28, 2005.

(51) Int. Cl.
*A61B 5/05* (2006.01)
(52) U.S. Cl. ........................ 600/430; 600/407
(58) Field of Classification Search ............. 600/430; 324/628; 702/1–189
See application file for complete search history.

(56) References Cited

U.S. PATENT DOCUMENTS

| | | | |
|---|---|---|---|
| 5,016,018 A | 5/1991 | Chang et al. | |
| 5,363,050 A | 11/1994 | Guo et al. | |
| 5,570,691 A | 11/1996 | Wright et al. | |
| 5,704,355 A | 1/1998 | Bridges | |
| 5,706,013 A | 1/1998 | Melvin et al. | |
| 5,807,257 A | 9/1998 | Bridges | |
| 5,829,437 A | 11/1998 | Bridges | |
| 5,942,899 A | 8/1999 | Shrekenhamer et al. | |
| 6,005,916 A | 12/1999 | Johnson et al. | |
| 6,061,589 A | 5/2000 | Bridges et al. | |
| 6,091,361 A | 7/2000 | Davis et al. | |
| 6,161,034 A | 12/2000 | Burbank et al. | |
| 6,421,550 B1 | 7/2002 | Bridges et al. | |
| 6,448,788 B1 * | 9/2002 | Meaney et al. | ............... 324/637 |
| 7,061,970 B2 | 6/2006 | Reed et al. | |

(Continued)

OTHER PUBLICATIONS

International Search Report dated Dec. 15, 2006 for PCT/US2006/004533.

(Continued)

*Primary Examiner*—Long V Le
*Assistant Examiner*—Angela M Hoffa
(74) *Attorney, Agent, or Firm*—Foley & Lardner LLP

(57) ABSTRACT

A method and a system of determining a surface location defining an interface between an object to image and an antenna is provided. The method uses geometric principles and the fact that an impedance mismatch at the interface results in significant reflection. A propagation time from the surface to each antenna of a plurality of antennas is estimated. The propagation time locates the surface on a circle centered at each antenna and having a radius calculated using the propagation time. A tangent line connects the intersection of adjacent circles with the surface. The surface is estimated to be located at the tangent point where the circle and the shared tangent line between adjacent antennas intersect. Multiple tangent points may be averaged for each interior antenna. A curve is fit to the set of tangent points to provide an estimate of the surface location.

20 Claims, 10 Drawing Sheets

U.S. PATENT DOCUMENTS

| | | | |
|---|---|---|---|
| 7,340,292 B2 * | 3/2008 | Li | 600/430 |
| 7,454,242 B2 * | 11/2008 | Fear et al. | 600/430 |
| 2002/0061280 A1 | 5/2002 | Mattrey | |
| 2002/0163480 A1 | 11/2002 | Eiges | |
| 2002/0197209 A1 | 12/2002 | Mattrey | |
| 2003/0088180 A1 * | 5/2003 | Van Veen et al. | 600/430 |
| 2004/0167399 A1 | 8/2004 | Li | |
| 2005/0251018 A1 | 11/2005 | Gleman | |
| 2005/0259621 A1 | 11/2005 | Lee | |
| 2006/0058606 A1 | 3/2006 | Davis et al. | |
| 2006/0183995 A1 | 8/2006 | Bond et al. | |
| 2007/0282200 A1 | 12/2007 | Johnson et al. | |

OTHER PUBLICATIONS

No-Weon Kang, et al., "A New 2-D Image Reconstruction Algorithm Based on FDTD and Design Sensitivity Analysis," IEEE Transactions on Microwave Theory and Techniques, vol. 50, No. 12, Dec. 2002, pp. 2734-2740.

Fear, Elise C., et al., "Microwaves for Breast Cancer Detection?" IEEE Potentials, Feb./Mar. 2003, pp. 12-18.

* cited by examiner

SURFACE IDENTIFICATION USING MICROWAVE SIGNALS FOR MICROWAVE-BASED DETECTION OF CANCER

CROSS-REFERENCES TO RELATED APPLICATIONS

This application claims priority to U.S. Provisional Application No. 60/648,295, filed Jan. 28, 2005, the entire disclosure of which is incorporated herein by reference in its entirety and for all purposes as if fully set forth herein.

REFERENCE TO GOVERNMENT RIGHTS

This invention was made with United States government support awarded by the following agencies: ARMY/MRMC DAMD 17-02-1-0625. The United States government has certain rights in this invention.

FIELD OF THE INVENTION

The present invention pertains generally to the field of imaging and more particularly to medical imaging using microwave transmissions to detect and to locate tumors in tissue.

BACKGROUND OF THE INVENTION

Various imaging techniques have been employed for detecting and locating cancerous tumors in body tissue. X-ray and ultrasound imaging techniques are commonly utilized in screening for breast cancer. X-ray mammography is the most effective current method for detecting early stage breast cancer. X-ray mammography, however, suffers from relatively high false positive and false negative rates, requires painful breast compression, and exposes the patient to low levels of ionizing radiation.

Microwave based imaging methods have been proposed for use in imaging of breast tissue and other body tissues as an alternative to current ultrasound and X-ray imaging techniques. Microwave imaging does not require breast compression, does not expose the patient to ionizing radiation, and can be applied at low power levels. Microwave-based imaging exploits the large contrast in dielectric properties between normal and malignant tissue. With microwave tomography, the dielectric-properties profile of an object being imaged is recovered from measurement of the transmission of microwave energy through the object. An alternative microwave imaging approach is based on radar methods that use the measured reflected signal to infer the locations of significant sources of scattering in the object being imaged. Radar methods require the focusing of the received signal in both space and time to discriminate against clutter and to obtain acceptable resolution. This may be accomplished with an antenna array and ultra-wideband microwave signals. For a discussion of this approach, see, S. C. Hagness, et al., "Two-Dimensional FDTD Analysis of a Pulsed Microwave Confocal System for Breast Cancer Detection: Fixed Focus and Antenna-Array Sensors," IEEE Trans. Biomed. Eng., Vol. 45, December, 1998, pp. 1470-1479; S. C. Hagness, et al., "Three-Dimensional FDTD Analysis of a Pulsed Microwave Confocal System for Breast Cancer Detection: Design of an Antenna-Array Element," IEEE Trans. Antennas and Propagation, Vol. 47, May, 1999, pp. 783-791; S. C. Hagness, et al., "Dielectric Characterization of Human Breast Tissue and Breast Cancer Detection Algorithms for Confocal Microwave Imaging," Proc. of the 2nd World Congress on Microwave and Radio Frequency Processing, Orlando, Fla., April, 2000; and X. Li, et al., "A Confocal Microwave Imaging Algorithm for Breast Cancer Detection," IEEE Microwave and Wireless Components Letters, Vol. 11, No. 3, March, 2001, pp. 130-132.

Alternative tumor detection and location methods have been proposed using radar methods. One method uses space-time beamforming. E. J. Bond, et al., "Microwave Imaging Via Space-Time Beamforming for Early Detection of Breast Cancer," IEEE Trans. Antennas and Propagation, Vol. 51, No. 8, August 2003. See also U.S. published patent application 2003/0088180 A1, "Space-Time Microwave Imaging for Cancer Detection," published May 8, 2003, the disclosure of which is incorporated herein by reference. As an alternative method, a generalized likelihood ratio test is used to detect and to locate possible tumors. See U.S. patent application Ser. No. 10/942,115, "Microwave-Based Examination using Hypothesis Testing," filed Sep. 15, 2004, the disclosure of which is incorporated herein by reference.

In implementing these microwave breast imaging methods, the breast surface defines the imaging domain of interest. Additionally, the reflection from the breast surface dominates the initial portion of the received signal and should be removed to allow for the detection and for the location of tumors within the breast tissue. As a result, a number of microwave breast imaging algorithms rely on a knowledge of the breast surface location relative to the transmitting and receiving antennas. Unfortunately, the location of the breast surface generally is unknown a priori, is expected to vary from patient to patient, and may vary from antenna to antenna depending on the arrangement of the antenna array. Therefore, it is desirable to be able to locate the position of each antenna relative to the breast surface. It is further beneficial to use the information available from the reflected microwave signals themselves to determine the location of the breast surface.

SUMMARY OF THE INVENTION

An exemplary embodiment of the invention relates to a system for determining a surface location of a 2-D cross section of a 3-D object. The surface defines an interface between an object to image and an antenna. The system includes, but is not limited to, a plurality of antennas, a receiver, and a processor. The receiver couples to the plurality of antennas to process received microwave signals thereby forming signal data. Processing of the signal data is carried out to obtain an image of the object. For example, in imaging the breast, each received signal contains contributions from antenna reverberations, the breast surface, clutter due to heterogeneity in the breast, reflection from possible lesions, and noise. Estimating the location of the breast surface using the reflected signals is needed to account for propagation effects in the design of high-performance lesion detection and imaging algorithms. The surface location must be determined because the surface location is unknown a priori and is expected to vary from patient to patient.

The surface location determination is based on geometric principles and the fact that the impedance mismatch at the breast surface results in significant backscatter or reflection. A propagation time from the antenna to the breast surface is determined using the significant backscatter or reflection from the breast surface. The propagation time to each antenna locates the breast surface on a circle with a radius calculated using the propagation time relative to each antenna location. The breast surface is assumed to be convex and tangent to the circle. A tangent point defines the intersection of the circle and the breast surface. The tangent point for each antenna is determined by assuming that the circles centered at adjacent antennas intersect the same tangent line. A tangent point is determined for each antenna location, and the resulting set of tangent points is fit with a curve. The resulting curve fit defines the surface location at any point along the 2-D cross section. A 3-D surface can be determined in a similar manner.

BRIEF DESCRIPTION OF THE DRAWINGS

FIG. 6 is a flow diagram illustrating exemplary operations of a breast surface estimation algorithm in accordance with the invention.

DETAILED DESCRIPTION OF THE INVENTION

Breast carcinomas act as significant microwave scatterers due to their large dielectric-property contrast with the surrounding tissue. Data in published literature and from our measurements on freshly excised breast biopsy tissue suggest that the malignant-to-normal breast tissue contrast in dielectric constant, $\in_r$, and conductivity, $\sigma$, is between 2:1 and 10:1, depending on the density of the normal tissue. The higher dielectric properties of malignant breast tissue arise, in part, from increased protein hydration and a breakdown of cell membranes due to necrosis. The contrast ratio does not vary significantly with tumor age, which suggests the potential for detecting tumors at the earliest stages of development. Preliminary measurements suggest that the contrast between the dielectric properties of normal breast tissue and many benign lesions is negligible, in which case benign lesions would not act as strong microwave scatterers, allowing discrimination of benign and cancerous lesions.

Microwaves offer exceptionally high contrast compared to other imaging modalities, such as X-ray mammography, which exploit intrinsic contrasts on the order of a few percent. Measurements suggest typical attenuation of microwave signals is less than 4 dB/cm up through 10 GHz, indicating that commercial microwave instrumentation with 100 dB of dynamic range is capable of imaging through 25 cm of tissue. In an exemplary embodiment, microwave pulses on the order of 100 ps in duration, with peak powers on the order of a few milliwatts—approximately $\frac{1}{100}^{th}$ of the power of a typical cellular phone can be used. Assuming a pulse repetition frequency of 1 MHz and a maximum scan depth of 10 cm, an array of 100 antennas can be sequentially scanned in 0.1 seconds.

The goal of conventional microwave tomography is the recovery of the dielectric-properties profile of an object from measurement of the transmission and scattering of microwave energy through the object. In contrast, microwave imaging using reflected signal power identifies the presence and the location of strong scatterers in the breast by directly imaging the reflected signal power. Early active microwave radar techniques were unsuccessful because they used a single antenna location for transmitting and receiving, and thus, had no possibility of spatially focusing the reflected signal. The use of an antenna array and short pulses enables focusing in both space and time. Thus, the system significantly enhances the response from malignant lesions while minimizing clutter signals, thereby overcoming challenges presented by breast heterogeneity and enabling the detection of lesions as small as 1-2 mm. As a result, resolution is not determined by the wavelength of the microwave excitation. Instead, the spatial extent of the array aperture measured in wavelengths and the temporal duration of the pulse dominate the factors determining the resolution limit.

Figure 1:
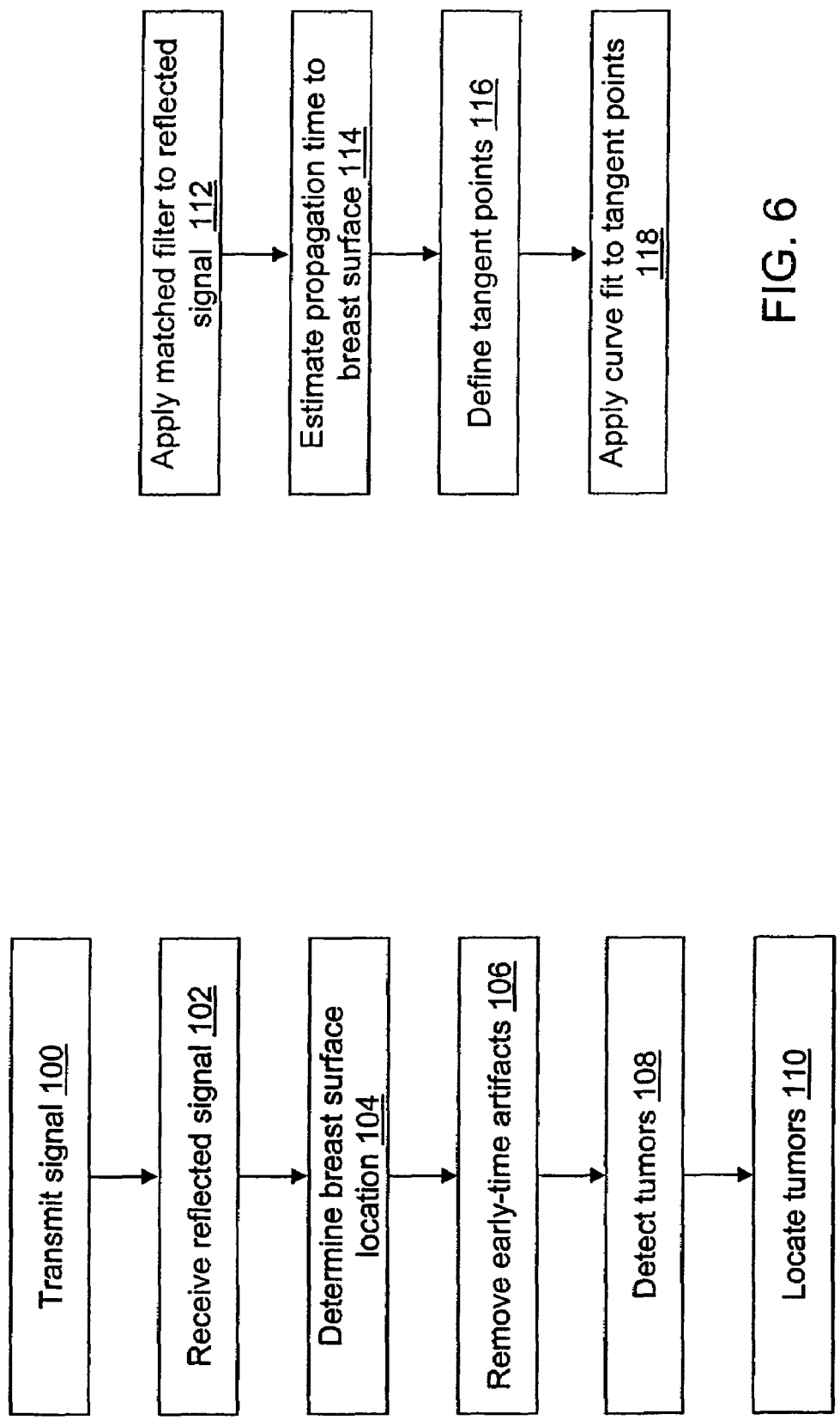
FIG. 1 is a flow diagram illustrating exemplary operations of a microwave imaging system in accordance with the invention.

With reference to FIG. 1, exemplary operations in a microwave imaging system are shown. In an operation 100, a microwave signal is transmitted from an antenna towards the area to be imaged, i.e. a breast. In an operation 102, a reflected signal from the transmitted microwave signal is received at an antenna or antennas. Using the received reflected signal, in an operation 104, the location of the breast surface relative to the antenna locations is determined. In an operation 106, the received reflected signal is processed to remove the early-time artifacts. Tumors are detected from the processed reflected signal in an operation 108. Detected tumors are located in an operation 110.

The invention can be practiced using various microwave imaging systems. In one embodiment for carrying out microwave imaging in accordance with the invention, each antenna in an array of antennas sequentially transmits a low-power, ultra-short microwave pulse into an object to be imaged, such as the breast, and receives the microwave signal reflected from the breast surface and the interior of the breast. In an alternative embodiment, each antenna in an array of antennas sequentially transmits wideband signals into an object to be imaged, such as the breast, and collects the resulting reflected signal. The relative arrival times and amplitudes of reflected signals received by the antennas across the antenna array provide information that can be used to detect the presence and determine the location of malignant lesions. The array of antennas may be linear, rectangular, circular, conformal, etc. The problem of detecting and localizing scattering objects using pulsed signals and antenna arrays is similar to that encountered in radar systems, such as those used for air traffic control, military surveillance, and land-mine detection. In still another alternative embodiment based on microwave tomography, one antenna of an array of antennas transmits a coherent microwave signal that is received by the remaining antennas after propagation through the object being imaged. The position of the transmitting antenna is changed and the process is repeated.

Figure 2:
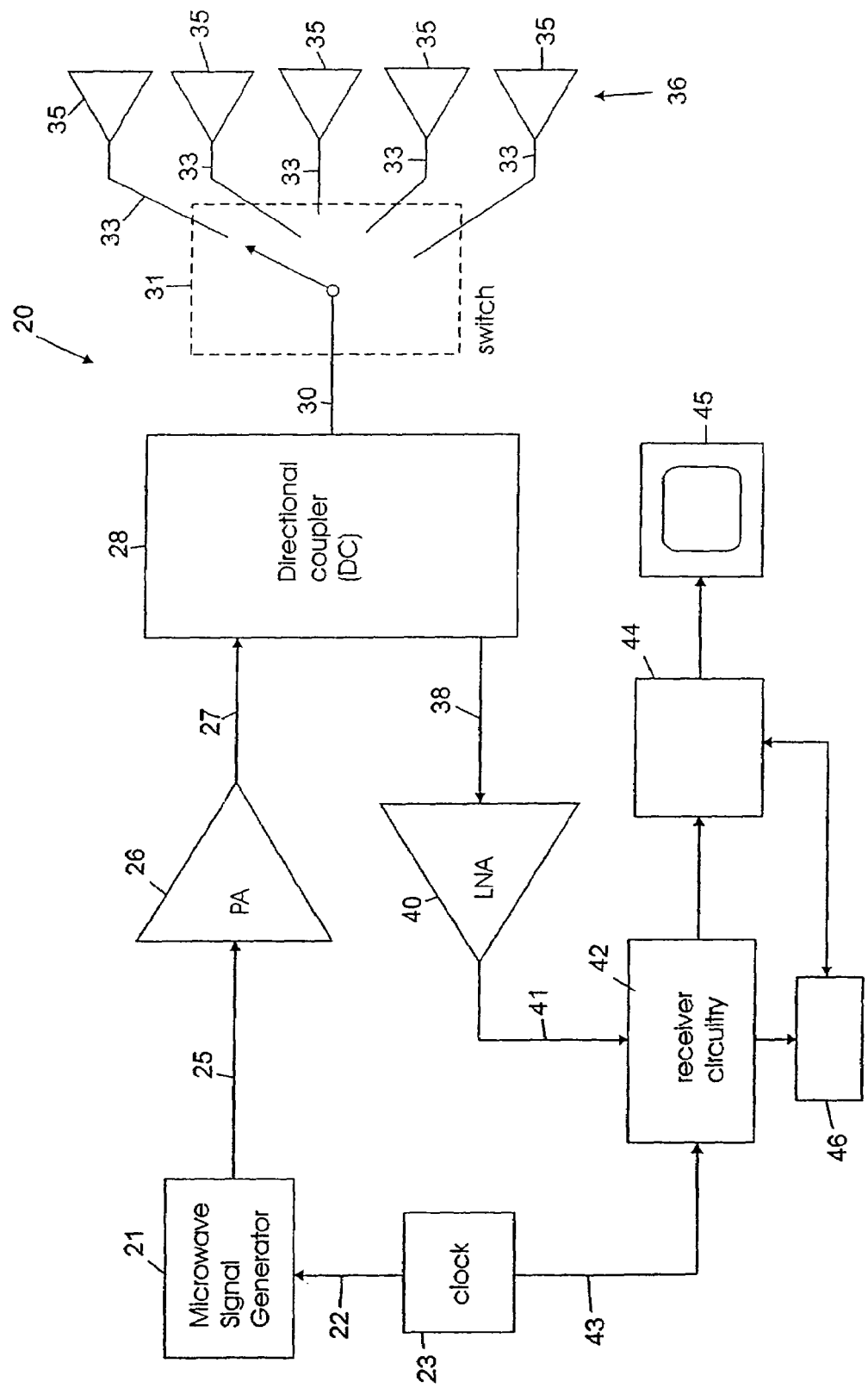
FIG. 2 is a block diagram of a microwave imaging system in accordance with the invention for transmitting and receiving using the same antenna.

With reference to FIG. 2, an exemplary microwave imaging system is shown. Transmission and reception of the microwave signals uses the same antenna and is shown generally at 20. The imaging system 20 includes a microwave signal generator 21 which is supplied, on a line 22, with clock pulses from a clock 23. The output of the signal generator 21, which as described below may be short broadband pulses or a signal synthesized from multiple discrete frequencies, from a frequency swept (chirp) pulse, etc., is provided on a line 25 to a power amplifier 26, the output of which is provided on a line 27 to a directional coupler 28. The output of the directional coupler 28 is provided on a line 30 to a switching system 31 which selectively directs the power from the line 30 to lines 33 leading to each of the antennas 35 which are arranged in an array 36 of antennas (e.g., a linear, a rectangular or a circular array).

An array of antennas may be synthesized by using one antenna 35 and moving it from position to position to collect data at each position, although the forming of a "virtual" array in this manner is not preferred. Further, the array may be formed to partially surround the object being imaged, for example, for use in breast imaging the array may be formed to encircle the pendant breast. The antennas 35 and other microwave components preferably should be wideband and operate in the 1-10 GHz range. Examples of wideband antenna designs that may be utilized are the "bowtie" and Vivaldi type antennas and horn antennas designed for wideband operation. See X. Li, et al, "Numerical and experimental investigation of an ultrawideband ridged pyramidal-horn antenna with curved launching plane for pulse radiation," IEEE Antennas and Wireless Propagation Letters, vol. 2, pp. 259-262, 2003.

The switch 31 is formed to selectively provide microwave power individually to the antennas 35 from the directional coupler 28 and to receive a signal from that antenna which is directed back through the switch 31 to the directional coupler 28. The directional coupler 28 sends the received signal on a line 38 to a low noise amplifier 40, the output of which is provided on a line 41 to a receiver 42. The receiver 42 also receives clock pulses on a line 43 from the clock 23. The clock pulses on the line 43 allow the receiver 42 to time the onset of pulses of microwave power supplied from the signal generator 21 to allow correlation in time of the received signal with respect to the transmitted signal. Alternatively, the power output from the signal generator 21 may be provided through a power splitter to the receiver 42 to allow time correlation.

The signal generator 21, which may include a computer or digital processor, generates appropriately timed and shaped output pulses, discrete frequencies, chirp pulses, etc., as required for the type of microwave transmission being utilized. The receiver 42 may be of conventional construction, providing detection of the received microwave signal and conversion of the detected signal to digitized data, e.g., with sampling of the received signal after each pulse to build up a digitized waveform, with the digitized data being provided to a digital signal processor of conventional design within the receiver 42 or to an appropriately programmed computer 44 (e.g., a general purpose PC, a dedicated digital signal processor, etc.) all of which will be referred to herein generally as a "processor." It is understood that any type of processor that can be programmed to carry out the signal/data processing set forth herein may be utilized. In accordance with the invention, the digitized data is used to determine the breast surface location.

The receiver 42 or the separate computer 44 additionally process the data to provide image data which may be displayed on a display device 45, such as a video display terminal, or which may be transmitted to a recording device 46 such as a magnetic disk or CD ROM for long-term storage, or transmitted for printout, further data processing, etc. A reflection artifact subtraction process (e.g., for the breast surface response or the antenna response) to reduce the effect of the early-time artifact response is performed on the received image data using signal processing techniques. The detection and location of tumors is carried out in a computer in the receiver 42 or a separate computer 44 on the processed data received from the antennas. Signal processing may also be carried out to compensate for frequency dependent scattering. As an example only of commercial instruments that may be utilized, the signal generator 21, amplifiers 26 and 40, directional coupler 28, receiver 42 and clock 23 may be implemented in an Agilent Vector Network Analyzer model 8720 ES, particularly for the discrete frequency based approach, and the computer 44 may be connected to control the signal generator 21 and the switch 31.

Figure 3:
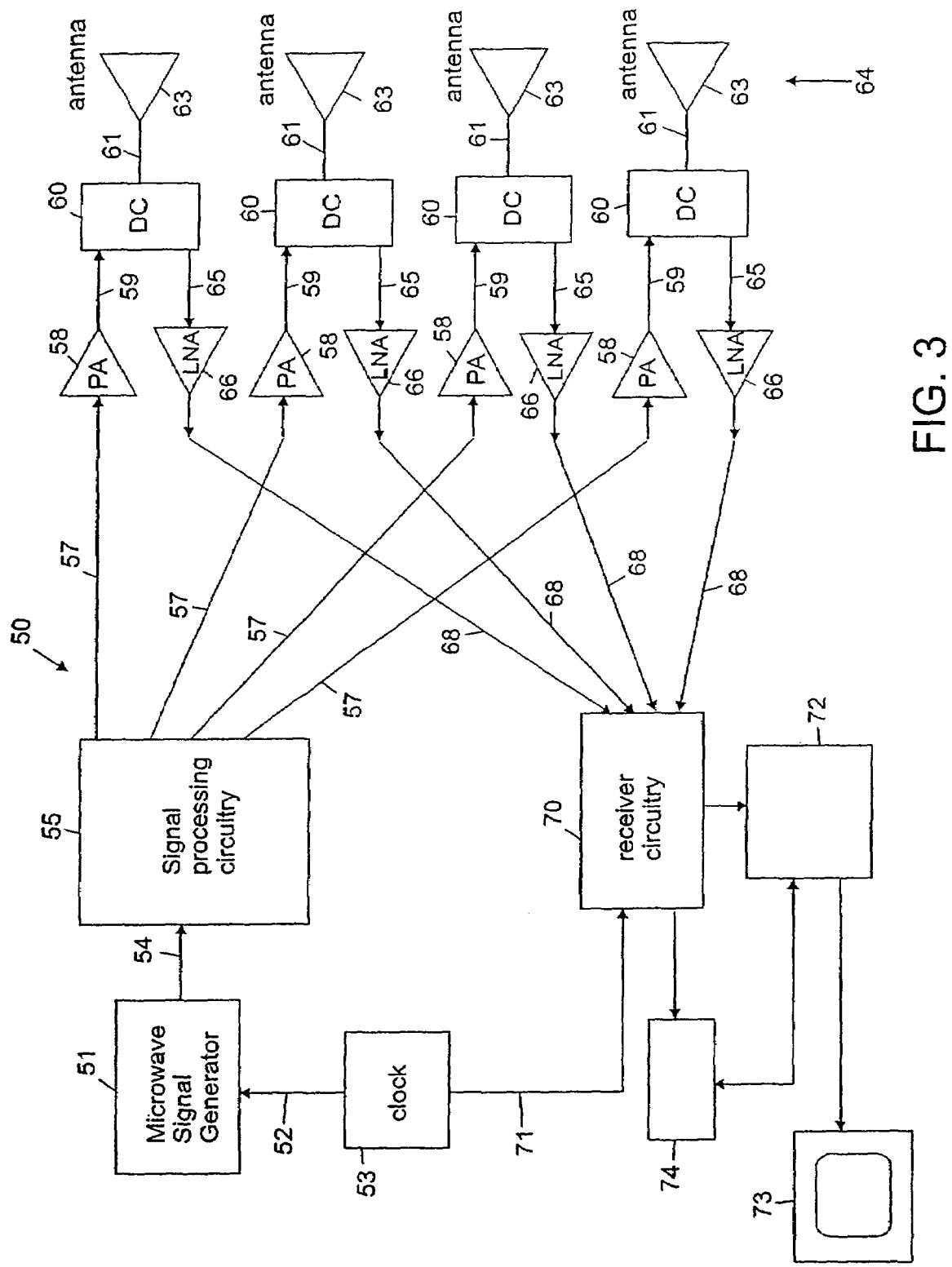
FIG. 3 is a block diagram of a further embodiment of a microwave imaging system in accordance with the invention providing simultaneous transmission and reception with all antennas.

A microwave imaging system which may be utilized for simultaneous transmission from each antenna is shown generally at 50 in FIG. 3. The system 50 includes a signal generator 51 which receives a clock pulse on a line 52 from a clock 53. The output of the signal generator 51 is provided on a line 54 to signal processing circuitry 55 which distributes the microwave (e.g., pulse) output on lines 57 to power amplifiers 58. Each of the power amplifiers 58 provides its output on a line 59 to a directional coupler 60, the output of which is provided on a line 61 to an individual antenna 63. The antennas 63 are arranged to form an array 64 of antennas, e.g., a rectangular array of antennas arranged in rows and columns.

The signal processing circuitry 55 distributes a microwave pulse on each of its output lines 57 with frequency dependent filtering to provide the desired microwave radiation from the antenna array 64, e.g., focusing of radiated power from the array 64 to selected points in the target object. The signals picked up by each antenna 63 are transmitted back on the line 61 to the directional coupler 60. The directional couplers provide the received signals on lines 65 to low noise amplifiers 66, the outputs of which are provided on lines 68 to a receiver 70. The receiver 70 also receives the clock pulses from the clock 53 on a line 71 to allow the receiver 70 to time the received signals with respect to the transmitted signals.

The receiver 70 detects the microwave signal on a line 68 and converts the received signal to digital waveform data which is processed by a digital signal processor or a computer 72 in accordance with the invention. The image data from the computer 72 or digital signal processor may be displayed, e.g., on a video display terminal 73, or provided to a storage device 74, e.g., CD ROM, magnetic disk, tape, etc. for long-term storage, or transmitted for other purposes. Breast surface location, reflection artifact removal (such as breast surface response removal), beam forming, tumor detection through hypothesis testing, frequency-dependent scattering processes, etc., may be carried out in a separate computer (e.g., the computer 44 of FIG. 2 or 72 of FIG. 3), or in a digital signal processor of the receiver (e.g., the receiver 42 of FIG. 2 or the receiver 70, of FIG. 3), both of which will be referred to herein as a processor, that is programmed to carry out the processing on the digitized waveform signal data for each antenna that is provided by the receiver.

Figure 4:
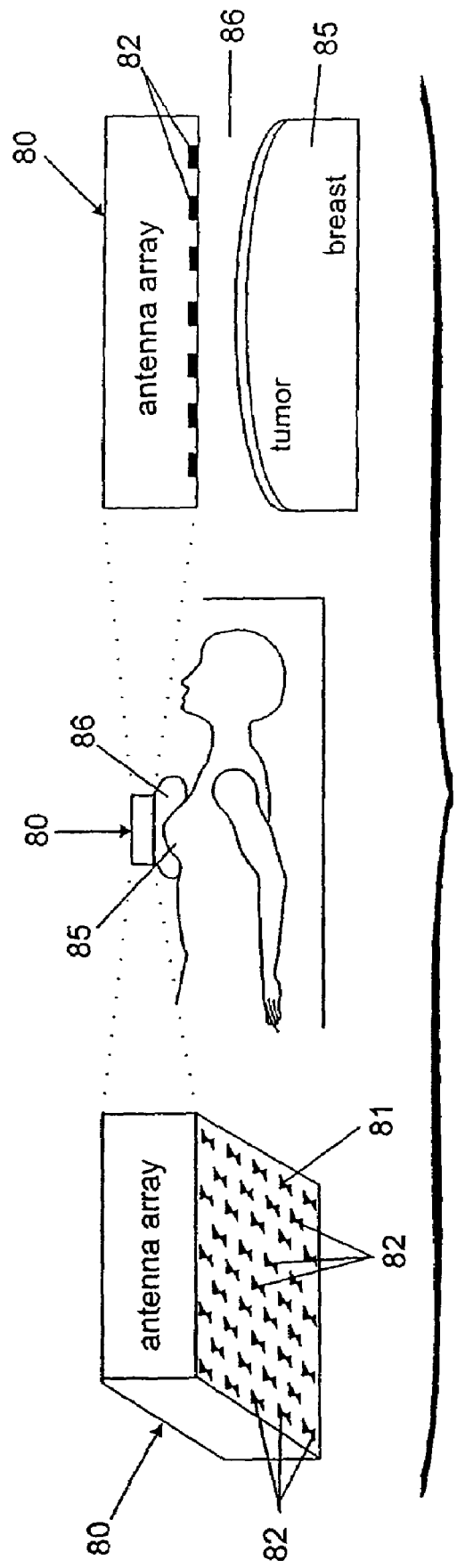
FIG. 4 is an illustrative view of an antenna array and its utilization in the microwave imaging system of the invention.

With reference to FIG. 4, an exemplary antenna array device which may be utilized in the microwave imaging system is shown generally at 80, having a face 81 over which are distributed multiple individual antennas 82 arranged in a two-dimensional array at known locations relative to each other. The individual antenna elements 82 may have the "bow-tie" shape as shown or other shapes as desired. The array device 80 may be utilized as the antenna array 36 of FIG. 2, with the antenna elements 82 corresponding to the antennas 35, or as the antenna array 64 of FIG. 3, with the antenna elements 82 corresponding to the antennas 63. For purposes of illustration, the antenna array device 80 is also shown in FIG. 4 placed adjacent to the breast 85 or other portion of the body to be imaged, preferably utilizing a matching element 86, such as a liquid filled bag, which conforms to the contour of the breast or other part of the body being imaged to minimize air gaps and unwanted reflections of microwave energy. While the invention is illustrated herein with regard to breast imaging, it is understood that the present invention may be utilized for imaging other parts of the body of an individual or other objects that may be separated from the microwave imaging system by a surface.

To achieve the best resolution of the reconstructed image, the radiated microwave pulse is preferably relatively short (e.g., about 100 ps), has a wide band of frequency content, typically from 0 to 20 GHz, with significant energy in the frequency range of 1 GHz to 10 GHz. It is desirable to utilize antennas that are suitable for transmitting and receiving such short pulses with minimum distortion or elongation. It is further desirable that the pulse radiating antenna have a constant sensitivity and a linear phase delay over the bandwidth of the incident electromagnetic pulse in the frequency domain. It is also desirable that the antenna design suppress both feed reflection and antenna ringing, and that the antenna have a smooth transition from the cable impedance at the feed point to the impedance of the immersion medium at the radiating end of the antenna. The return loss, S11, should be low in magnitude as less return loss means more power is transmitted to the antenna. Ideally, the return loss should be constant over the required bandwidth so that the spectrum of the transmitted power is flat and should have a linear phase delay across the frequency band so that the radiated waveform will not be dispersed. Other desirable properties include a well-defined polarization, constant gain, and low side lobes in the radiation pattern. Resistively loaded cylindrical and conical dipole (monopole), and bow-tie antennas can be utilized for radiating temporally short, broad bandwidth pulses. Resistive loading can be utilized to reduce the unwanted reflections that occur along the antenna and the associated distortion of the radiated signal. Spiral antennas and log-periodic antennas have also been designed to achieve wide bandwidth. Spectrum shaping and RF filtering may be needed to enhance the frequency performance of these antennas. Specialized antennas designed for pulse radiation may also be utilized. An example of a suitable antenna that is designed for short pulse radiation is shown and described in U.S. Pat. No. 6,348,898, issued Feb. 19, 2002.

The methods described above assume only one antenna is transmitting and receiving at any point in time. This process involves sequentially stepping through the array. If an antenna array with multiple receive channels is used as shown in FIG. 3, then a multitude of different transmit-receive strategies are possible. Tumor detection/location and breast surface response removal algorithms may be utilized in which all antennas receive simultaneously. Transmit strategies may also be utilized that focus the transmitted energy on a given region of the breast. The transmit and receive focus location is then scanned throughout the breast to form the image of scattered power. Such scanning may be utilized to improve resolution and robustness to artifacts, noise, and clutter. The signal parameters used to focus the transmission are the relative transmit time and signal amplitude in each antenna. After a lesion is located, the transmitted energy from the antennas may be focused on the lesion at a higher power level to heat and destroy the lesion.

An exemplary sensor in the imaging system may include a microwave vector reflectometer (the pulse generator 21, 51 and receiver 42, 70, and may include the associated amplifiers and directional couplers) and a low-reverberation ultrawideband transmitting/receiving antenna. A low-noise commercial vector network analyzer (VNA) with a time-domain option may be used for the vector reflectometer. The dynamic range of a VNA of this type is sufficient to detect small malignant tumors up to depths of 5.0 cm in the breast.

Figure 5:
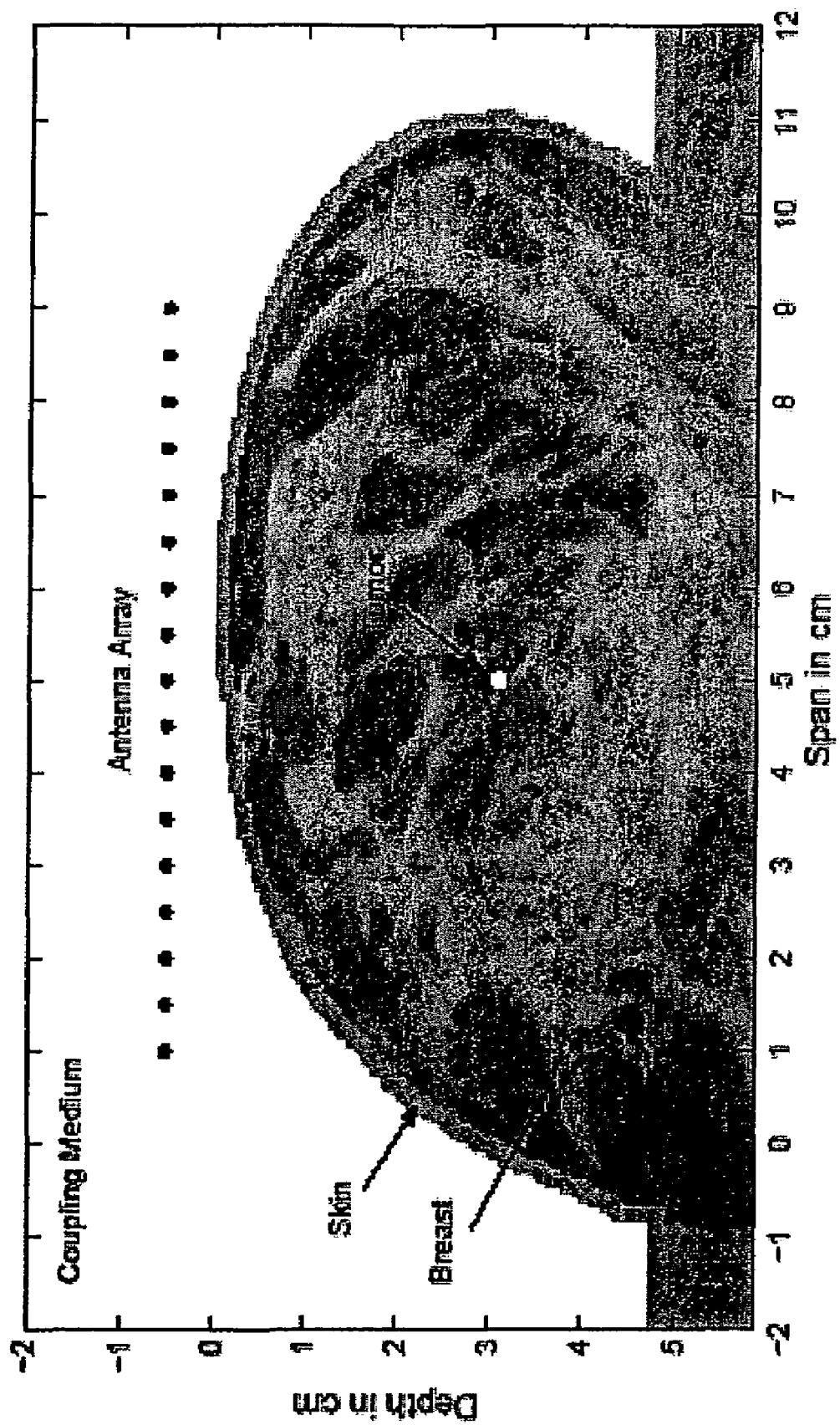
FIG. 5 is 2-D Magnetic Resonance Image (MRI) derived finite-difference time-domain breast model for a patient lying in the supine position.

With reference to FIG. 5, a 2-D sample array configuration relative to a breast is shown. The breast is immersed in a coupling medium matched to the breast surface layer. In a supine configuration, a uniform linear array is placed near the surface of the naturally flattened breast. To approximate the supine configuration in 2-D, a sagittal plane through the breast with antennas positioned near the top of the breast, as shown in FIG. 5, is used. The grayscale display of the interior of the breast shows the anatomically realistic variation of the permittivity within the breast as derived from the density variation of a high-resolution breast MRI data set. Lighter regions represent higher dielectric-property values of denser fibroglandular tissue while the darker regions represent lower dielectric-property values of less dense adipose tissue.

As summarized with reference to FIG. 1, microwave signals are received at an antenna where the transmitting antenna may or may not be the same as the receiving antenna. Processing of the received signals is carried out to obtain an image of microwave energy. Each received signal contains contributions from antenna reverberations, the breast surface, clutter due to heterogeneity in the breast, reflection from possible lesions, and noise. The location of the breast surface relative to the antennas is needed to account for propagation effects in the design of high-performance lesion detection and imaging algorithms. This information is unknown a priori and is expected to vary from patient to patient.

Figure 7:
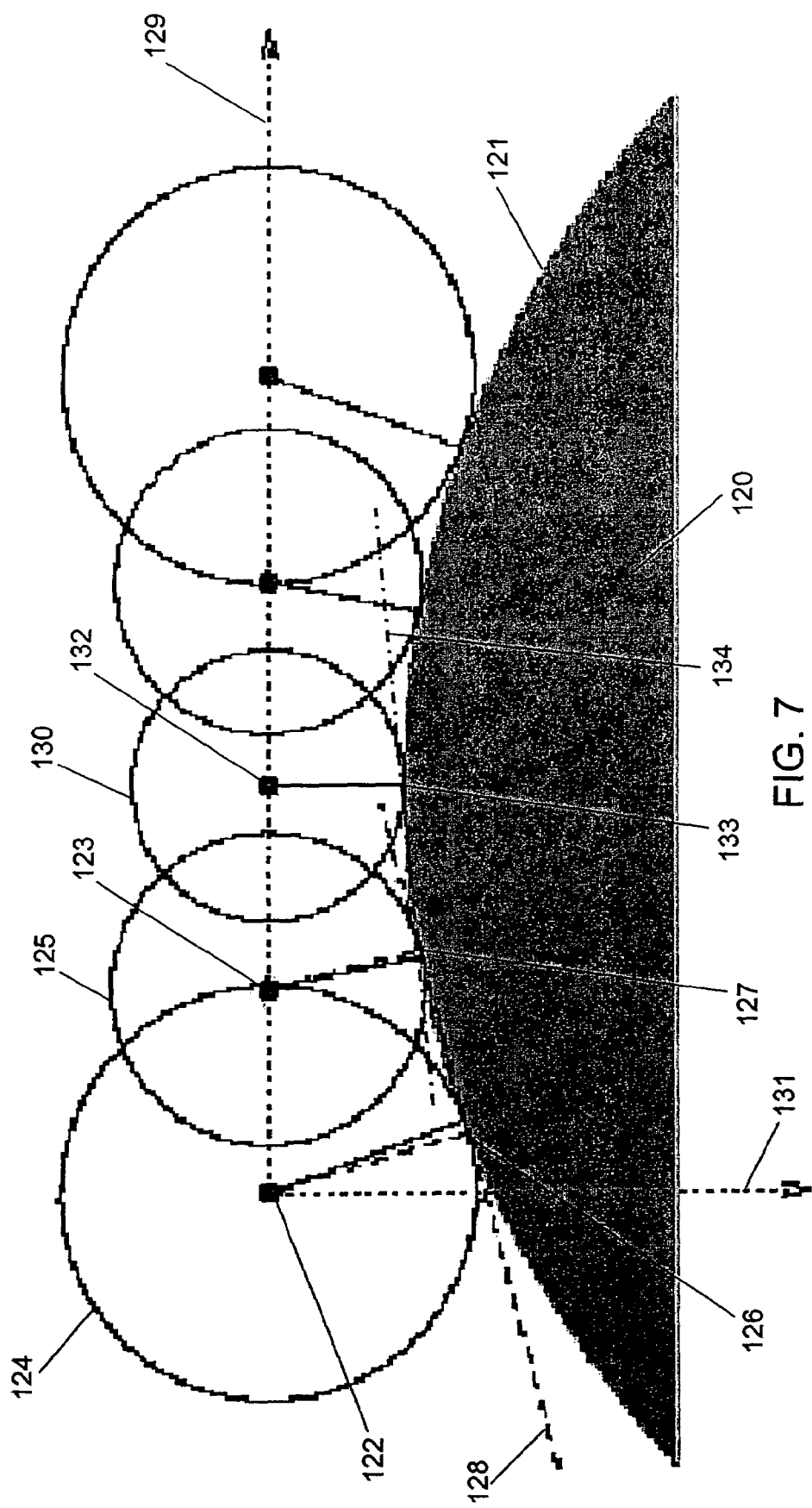
FIG. 7 is an illustration depicting a portion of the breast surface estimation algorithm in accordance with the invention.

With reference to FIG. 6, exemplary operations of the breast surface determination process are shown for a 2-D cross section of a 3-D object. The process is based on geometric principles and the fact that the impedance mismatch at the breast surface results in significant backscatter or reflection. In an operation 112, a matched filter is applied to the reflected signal received in each antenna channel. In an operation 114, the output of the matched filter is used to estimate the propagation time from the antenna to the breast surface. In alternative embodiments, other techniques may be used to estimate the propagation time from the antenna to the breast surface. The propagation time locates the breast surface on a circle with known radius, as shown in FIG. 7. The breast surface is assumed to be convex and tangent to the circle of known radius. A tangent point defines the intersection of the circle and the breast surface. In an operation 116, the tangent point for each antenna is determined by assuming that the circles centered at adjacent antennas are located on the same tangent line defined by the tangent points. This is a very good approximation if the antennas are sufficiently closely spaced relative to the curvature of the breast surface. The breast surface is estimated to be located at the point where the circle and tangent line touch. Multiple tangent points are obtained for each interior antenna because of pairings with multiple adjacent antennas. In these cases, an average tangent point is calculated using the tangent point for each of the multiple adjacent antennas. The average tangent point is used as the estimate of the breast surface location in these cases. In an operation 118, a curve fit is defined, as known to those skilled in the art, using the defined tangent points that are saved in a data set. The resulting curve fit defines the breast surface location at any point along the 2-D cross section.

The antenna array is assumed to be one-dimensional, off the breast surface, and planar as shown in FIG. 7. It is also assumed that the waves radiating from each antenna are cylindrical and isotropic and that the medium that the antenna array is submersed in is the same material that makes up the breast surface skin layer. In a 2-D setting, these signals can be viewed as outwardly growing concentric circles, and for each antenna, the point that these circles are tangent with the breast surface can be estimated by following the shortest straight-line path from the antenna location to the interface. Based on geometry, this shortest path is the radius of the circle positioned at an angle from the x-axis 129 allowing for the tangent line to the circle to also be tangent to the breast surface. The 2-D cross section is defined by the x-axis 129 and a y-axis 131. Because the breast surface is convex, the location on the breast surface giving the shortest path to the antenna of interest is unique. FIG. 7 illustrates this shortest path with the circle tangent to the breast surface and its radius denoted with a solid line.

The minimal distance from each antenna to the breast surface is calculated by using the reflection due to the breast surface to estimate the round-trip time delay and multiplying this time delay by the average velocity of the signals in the skin medium. For example, the time-delay may be estimated by matched-filtering the transmitted signal with each received waveform. Knowing the estimate of the minimal distance is equivalent to knowing the radius of a circle with a center at the location of the transmitting antenna. FIG. 7 shows the breast surface along with each circle centered at a transmitting antenna location. It can be seen from the figure that each circle is tangent to the breast surface. The location is approximated with the unique position that allows for the line tangent to the circle at that position to also be tangent to the adjacent circle. The dashed radial lines have endpoints at these tangential locations. The solid radial lines have endpoints at the breast surface. It can be seen that the approximation error between the actual and estimated tangential points is quite small.

With reference to FIG. 7, the determination of the tangent points for a pair of adjacent antennas in 2-D is described. A breast 120 is surrounded by a breast surface 121. As shown with reference to FIG. 7, a row of antennas includes a first antenna 122 and a second antenna 123 adjacent the first antenna 122. A first circle 124 surrounds the first antenna 122 and a second circle 125 surrounds the second antenna 123. The line 128 is tangent to both the first circle 124 and the second circle 125 and passes through a first point $(x_1, y_1)$ 126 on the first circle 124 and a second point $(x_2, y_2)$ 127 on the second circle 125. Each solid radial line shown in FIG. 7 terminates at the point where the breast surface and the circle are tangent. The two dashed radial lines are orthogonal to line 128 illustrating that the error between the true and the estimated tangent points is small. Letting h denote the inter-element spacing between the antennas and r1 and r2 denote the radial distance for the first circle 124 and the second circle 125, respectively, the slope of the tangent line to each circle can be derived using calculus to be $$m_1 = \frac{-x_1}{\sqrt{r_1^2 - x_1^2}}$$

and $$m_2 = \frac{h - x_2}{\sqrt{r_2^2 - (x_2 - h)^2}}.$$

This allows for the equation of the tangent line to each circle to be written as $$y_1 = m_1 x_1 + b_1 = \frac{-x_1}{\sqrt{r_1^2 - x_1^2}} x_1 + b_1 \quad (1)$$

$$y_2 = m_2 x_2 + b_2 = \frac{h - x_2}{\sqrt{r_2^2 - (x_2 - h)^2}} x_2 + b_2 \quad (2)$$

where b1 and b2 are the y-intercepts. The constraint of using the line simultaneously tangent to both circles implies that m1=m2 and b1=b2=b. Setting m1=m2 yields the following relation between x1 and x2:

$$x_2 - h = \frac{x_1 r_2}{r_1} \quad (3)$$

By setting b in (1) and (2) equal to each other, some algebraic manipulation with usage of (3) yields the following equation for $x_1$, $$x_1 = \frac{r_1^2 - r_2 r_1}{h} \quad (4)$$

The y-coordinate, $y_1$, can naturally be calculated using the equation of the circle for first circle 124.

As shown with reference to FIG. 7, a third antenna 132 is adjacent the second antenna 123. A third circle 130 surrounds the third antenna 132. The line 134 is tangent to both the second circle 125 and the third circle 130 and passes through a third point (x3, y3) 133 on the third circle 130 and a fourth point (x2', y2') on the second circle 125. The process described above relative to the first point (x1, y1) 126 and the second point (x2, y2) 127 is used to calculate the fourth point (x2', y2') and the location of the third point (x3, y3) 133. The point used to estimate the location of the surface below the second antenna 123 is the average of the second point (x2, y2) 127 calculated using the first circle 124 and the fourth point (x2', y2') calculated using the third circle 130. This process is repeated for each of the antennas in the array averaging for interior antennas. The calculations may be initiated from any antenna in the array.

After determining each estimated tangent point (using the average of the tangent points for the interior antennas), a curve is fit to the estimated tangent points. The curve fit should approximate the breast shape. In an exemplary embodiment, the curve fit is a cubic B-spline. The cubic B-spline provides a good approximation to the convex shape of the breast. Other curve fits may be used in alternative embodiments.

Figure 8:
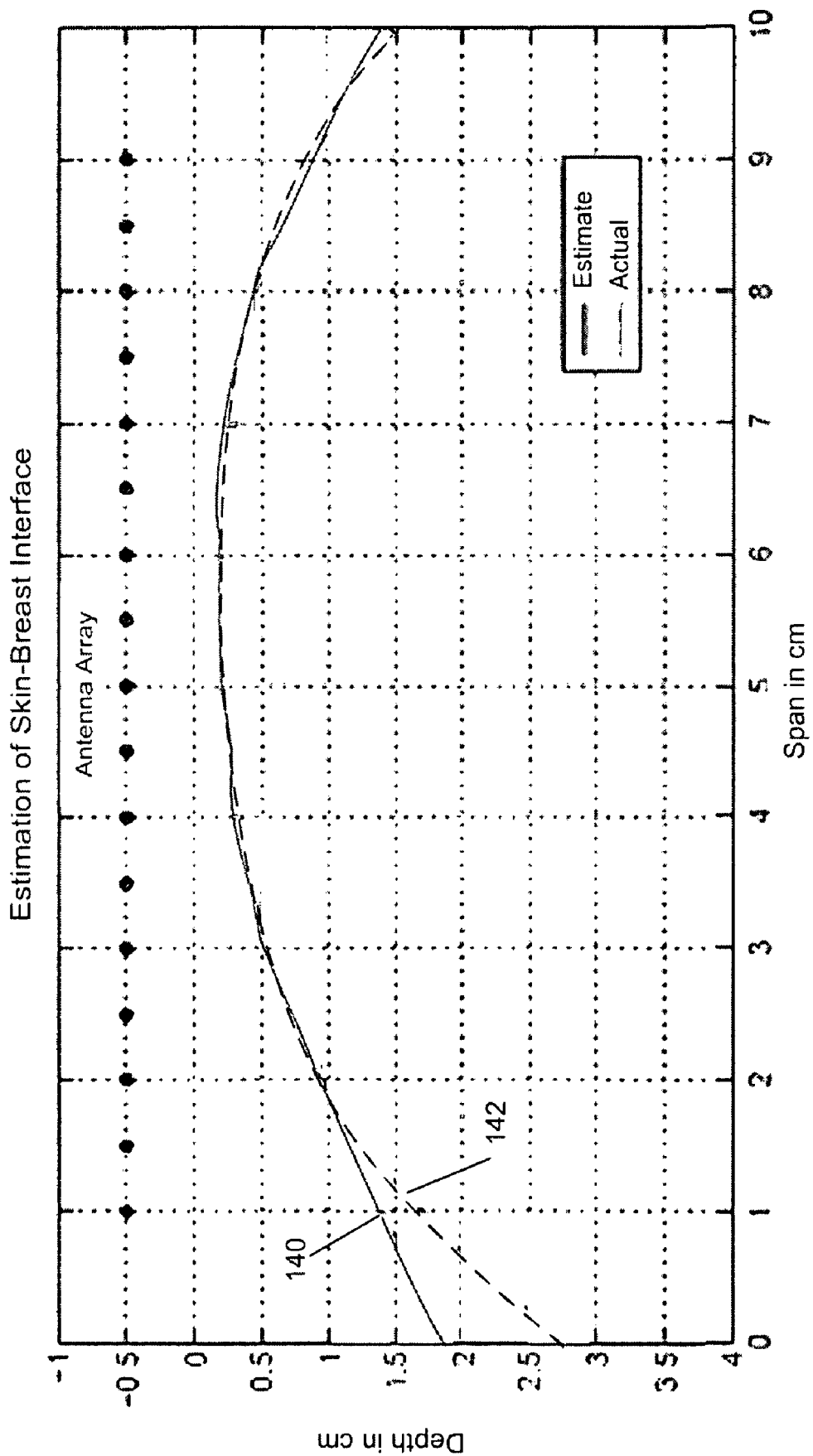
FIG. 8 is an illustration representing 2-D cross sectional results from the breast surface estimation algorithm as compared to the actual breast surface location.

FIG. 8 illustrates the performance of the breast surface identification algorithm when the patient is in the supine position for a 2-D cross section of the 3-D breast. The estimate curve 140 represents the estimate of the breast surface while the actual curve 142 represents the actual breast surface. A cubic B-spline was fit through the estimated tangent points to approximate the breast surface. There is excellent agreement between the estimated and the actual interface although accuracy suffers outside the array aperture, as expected. Similar quality results are obtained in the prone configuration.

In a similar manner as described above, a 3-D surface can be determined. In an experimental configuration, the patient was assumed to lie in the prone position with the breast immersed in a bolus of oil. The breast was assumed to be homogeneous and was modeled as a hemi-ellipsoid. A circular ring of eight horn antennas surrounded the pendulous breast at three different depths with 1.5 cm spacing. Although the waves that are radiated from the horn antennas are directional, the radiation pattern can be assumed to be omnidirectional so that the circle/tangent line approach remains valid. The breast surface identification algorithm locates the surface in various 2-D cross-sections of the breast allowing for a 3-D surface to be reconstructed from these cross-sections. Each vertical array of three collinear antennas and the center of the circular array defines a 2-D plane for surface identification.

The time delay used to calculate the minimal distance from each antenna to the skin surface can be estimated from the received data by any number of methods. One such method that yields accurate time-delay estimates involves using the squared difference between delayed versions of the incident (transmitted) signal and the received signal as an estimation criterion. Let $p(m)$ and $b_i(m)$ represent the incident pulse and the received signal at the ith antenna, respectively. The time delay $D_i$ associated with antenna i can be estimated as that delay where the first minimum of the following residual $e(D)$ occurs:

$$e(D) = \Sigma_m |p(m-D) - b_i(m)|^2 \quad (5)$$

The location of the minimum can determined by locating the first zero crossing of the derivative of $e(D)$.

Figure 9:
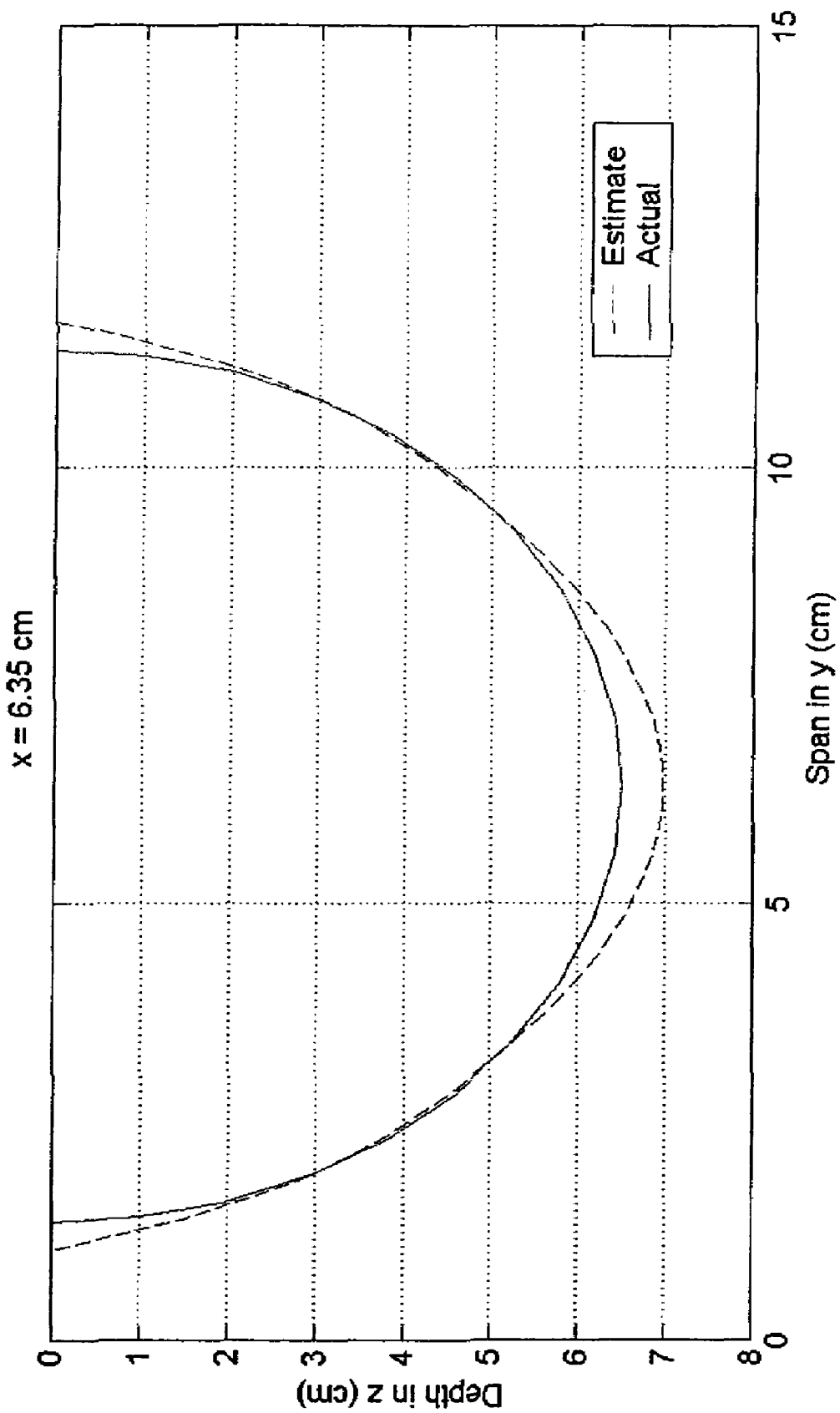
FIG. 9 is an illustration representing a 2-D y-z cross sectional result from the breast surface estimation algorithm as compared to the actual breast surface location using a 3-D object.
Figure 10:
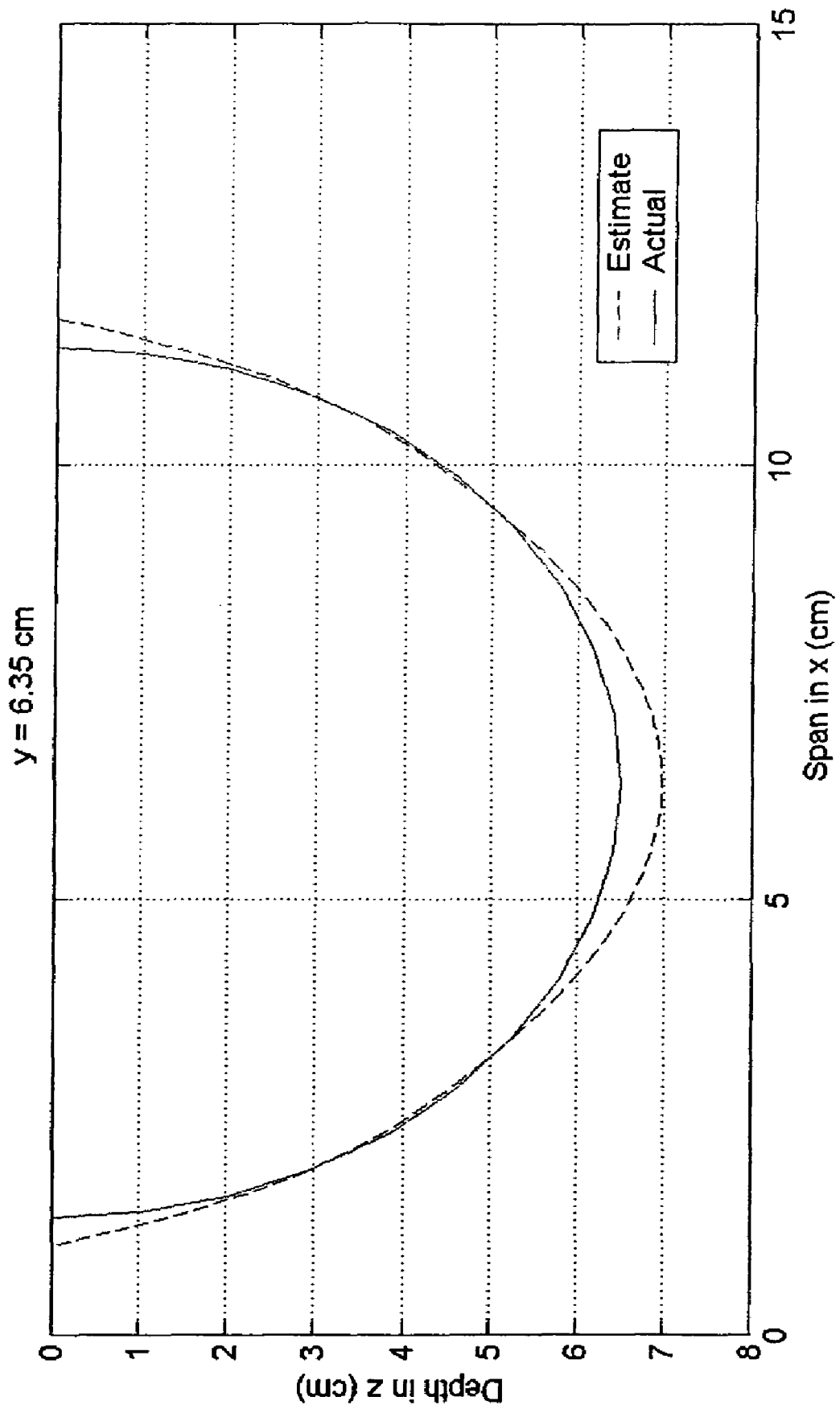
FIG. 10 is an illustration representing a 2-D x-z cross sectional results from the breast surface estimation algorithm as compared to the actual breast surface location using a 3-D object.
Figure 11:
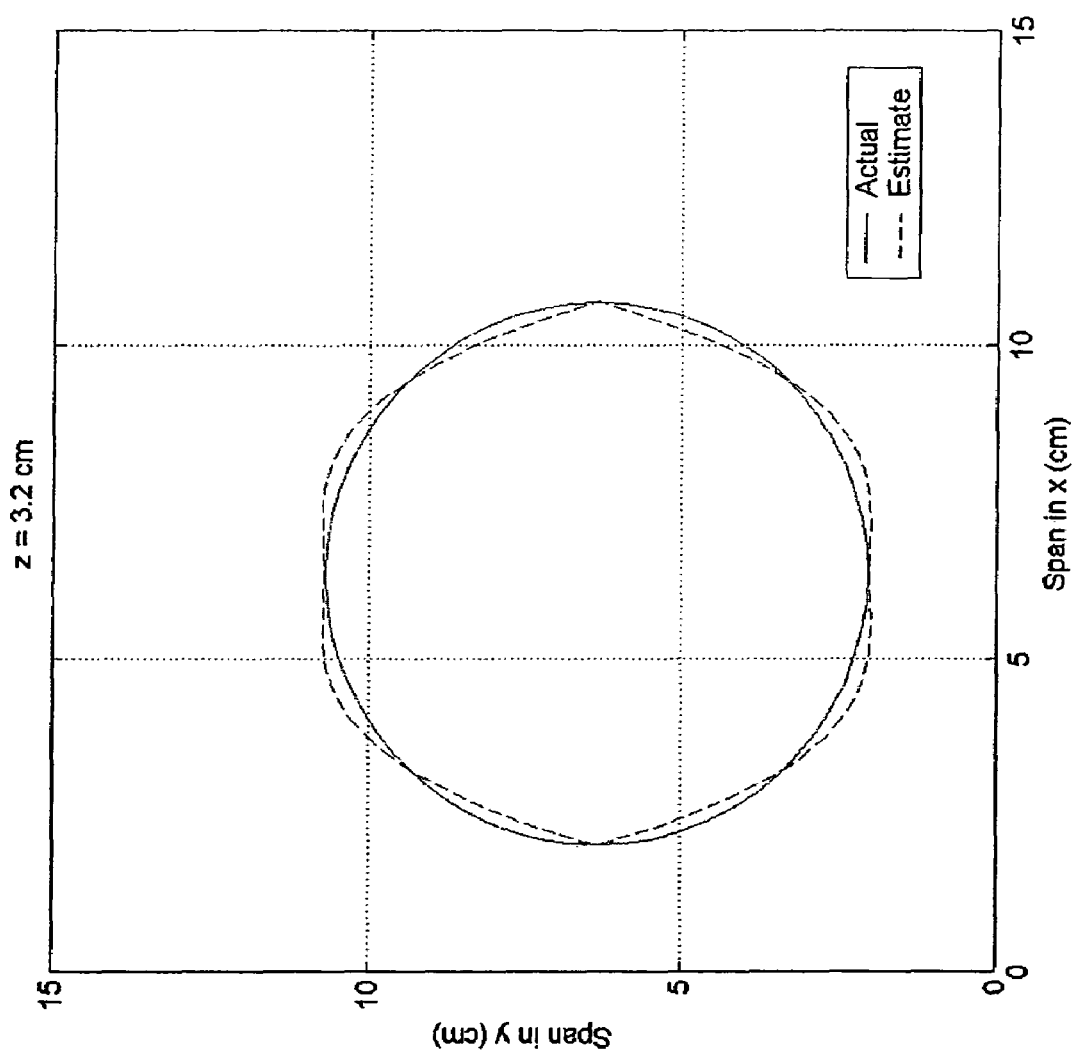
FIG. 11 is an illustration representing a 2-D x-y cross sectional results from the breast surface estimation algorithm as compared to the actual breast surface location using a 3-D object.

FIGS. 9-11 illustrate the performance of the breast surface identification algorithm for the 3-D case under the experimental configuration by showing the estimated and actual curves of the surface in three orthogonal planes. The three orthogonal planes are labeled using x- and y-axes that correspond to the lateral dimensions and a z-axis that corresponds to the depth dimension. A cubic B-spline was fit through the estimated tangent points to approximate the skin surface in each plane. As shown in FIGS. 9-11, there is excellent agreement between the actual and estimated surface over the range covered by the three rings of antennas (z=2.65 cm to 5.65 cm), though errors occur outside the array aperture, as expected.

It is understood that the invention is not limited to the embodiments set forth herein for purposes of illustrating the invention, but embraces all such forms thereof as come within the scope of the following claims.

What is claimed is:

1. A system for determining a two-dimensional cross section of a surface location that defines an interface between an object to detect and an antenna, the determination of the surface location for use in an imaging system, the system comprising:
   a plurality of antennas;
   a receiver coupled to the plurality of antennas, the receiver defining signal data from a signal received by at least one antenna of the plurality of antennas; and
   a processor operably coupled to the receiver to receive the defined signal data, the processor configured to execute computer-readable instructions configured to cause the system to
   (a) estimate, from the signal data, a first minimum propagation time for a first signal received at a first antenna, the first signal reflected from a surface, wherein the first antenna is one of the plurality of antennas;
   (b) calculate a first distance between the surface and the first antenna using the estimated first minimum propagation time;
   (c) define a first circle centered at the first antenna, the first circle having a first radius equal to the calculated first distance;
   (d) estimate, from the signal data, a second minimum propagation time for a second signal received at a second antenna, the second signal reflected from the surface, wherein the second antenna is one of the plurality of antennas and is adjacent a transmit location of the first antenna;
   (e) calculate a second distance between the surface and the second antenna using the estimated second minimum propagation time;
   (f) define a second circle centered at the second antenna, the second circle having a second radius equal to the calculated second distance;
   (g) define a tangent point, the tangent point located on the first circle and on a line tangent to both the first circle and the second circle and in a direction of radiation of the first antenna toward the surface;
   (h) save the defined tangent point in a set of tangent points;
   (i) repeat steps (a)-(h) for the first antenna being each of the plurality of antennas; and
   (j) determine a location of the surface by applying a curve fit to the set of tangent points.

2. The system of claim 1, wherein at least one of the plurality of antennas transmits a transmit signal selected from the group consisting of a short broadband pulse, a pulse synthesized from a plurality of discrete frequencies, and a frequency swept pulse.

3. The system of claim 1, wherein at least one of the plurality of antennas transmits a wideband signal.

4. The system of claim 3, wherein the wideband signal has a frequency in the range of one to ten gigahertz.

5. The system of claim 1, wherein at least one of the plurality of antennas transmits a coherent signal.

6. The system of claim 1, wherein the plurality of antennas are arranged to form a rectangular array.

7. A microwave imaging system for detecting an object, the system comprising:
   a plurality of antennas;
   a receiver coupled to the plurality of antennas, the receiver defining signal data from a signal received by at least one antenna of the plurality of antennas; and
   a processor operably coupled to the receiver to receive the defined signal data, the processor configured to execute computer-readable instructions configured to cause the system to
   (a) estimate, from the signal data, a first minimum propagation time for a first signal received at a first antenna, the first signal reflected from a surface, wherein the first antenna is one of the plurality of antennas;
   (b) calculate a first distance between the surface and the first antenna using the estimated first minimum propagation time;

(c) define a first circle centered at the first antenna, the first circle having a first radius equal to the calculated first distance;

(d) estimate, from the signal data, a second minimum propagation time for a second signal received at a second antenna, the second signal reflected from the surface, wherein the second antenna is one of the plurality of antennas and is adjacent a transmit location of the first antenna;

(e) calculate a second distance between the surface and the second antenna using the estimated second minimum propagation time;

(f) define a second circle centered at the second antenna, the second circle having a second radius equal to the calculated second distance;

(g) define a tangent point, the tangent point located on the first circle and on a line tangent to both the first circle and the second circle and in a direction of radiation of the first antenna toward the surface;

(h) save the defined tangent point in a set of tangent points;

(i) repeat steps (a)-(h) for the first antenna being each of the plurality of antennas;

(j) determine a location of the surface by applying a curve fit to the set of tangent points; and (k) detect an object using the signal data, wherein the object is located on a side of the determined location of the surface opposite the plurality of antennas.

8. The microwave imaging system of claim 7, wherein the computer-readable instructions further cause the system to remove a portion of the signal data associated with the determined location of the surface.

9. The microwave imaging system of claim 7, wherein the object is a tumor.

10. A computer implemented method of determining a two-dimensional cross section of a surface that defines an interface between an object to image and an antenna, the determination of the surface location for use in an imaging system, the method comprising:

(a) using a processor of a computer, estimating a first minimum propagation time for a first signal received at a first antenna, the first signal reflected from a surface, wherein the first antenna is one of a plurality of antennas;

(b) using a processor of a computer, calculating a first distance between the surface and the first antenna using the estimated first minimum propagation time;

(c) using a processor of a computer, defining a first circle centered at the first antenna, the first circle having a first radius equal to the calculated first distance;

(d) using a processor of a computer, estimating a second minimum propagation time for a second signal received at a second antenna, the second signal reflected from the surface, wherein the second antenna is one of the plurality of antennas and is adjacent a transmit location of the first antenna;

(e) using a processor of a computer, calculating a second distance between the surface and the second antenna using the estimated second minimum propagation time;

(f) using a processor of a computer, defining a second circle centered at the second antenna, the second circle having a second radius equal to the calculated second distance;

(g) using a processor of a computer, defining a tangent point, the tangent point located on the first circle and on a line tangent to both the first circle and the second circle and in a direction of radiation of the first antenna toward the surface;

(h) using a processor of a computer, saving the defined tangent point in a set of tangent points;

(i) using a processor of a computer, repeating steps (a)-(h) for the first antenna being each of the plurality of antennas; and (j) using a processor of a computer, determine a location of the surface by applying a curve fit to the set of tangent points.

11. The method of claim 10, further comprising before (h):

(k) using a processor of a computer, repeating (d)-(g) for the second antenna being each antenna of the plurality of antennas that is adjacent the first antenna; and (l) using a processor of a computer, calculating an average of the defined tangent point for each repetition of (k), wherein the defined tangent point saved in step (h) is the calculated average.

12. The method of claim 10, wherein the curve fit is a cubic spline.

13. The method of claim 12, wherein the cubic spline is a cubic B-spline.

14. The method of claim 10, further comprising before (a):
using a processor of a computer, applying a matched filter to the received first signal forming a filtered signal, wherein estimating the first minimum propagation time uses the filtered signal.

15. The method of claim 10, wherein the surface is a skin surface of an animal.

16. The method of claim 15, wherein the skin surface covers at least a portion of a breast of the animal.

17. The method of claim 10, wherein the tangent point is defined as $(x_1, y_1)$ and defining the tangent point comprises solving the equations $$x_1 = \frac{r_1^2 - r_2 r_1}{h}$$

and $y_1 = \sqrt{r_1^2 - x_1^2}$, where $r_1$ is the first radius, $r_2$ is the second radius, and $h$ is a distance between the first antenna and the second antenna.

18. A storage device having computer-readable instructions stored thereon that, upon execution by a processor, cause a device to:

(a) estimate, from signal data collected from a plurality of antennas and stored on the storage device, a first minimum propagation time for a first signal of the signal data, wherein the first signal represents a reflection from a surface received at a first antenna of the plurality of antennas;

(b) calculate a first distance between the surface and the first antenna using the estimated first minimum propagation time;

(c) define a first circle centered at the first antenna, the first circle having a first radium equal to the calculated first distance;

(d) estimate, from the signal data, a second minimum propagation time for a second signal of the signal data, wherein the second signal represents a second reflection from the surface received at a second antenna of the plurality of antennas adjacent a transmit location of the first antenna;

(e) calculate a second distance between the surface and the second antenna using the estimated second minimum propagation time;

(f) define a second circle centered at the second antenna, the second circle having a second radius equal to the calculated second distance;

(g) define a tangent point, the tangent point located on the first circle and on a line tangent to both the first circle and the second circle and in a direction of radiation of the first antenna toward the surface;

(h) save the defined tangent point in a set of tangent points;

(i) repeat steps (a)-(h) for the first antenna being each of the plurality of antennas; and (j) determine a location of the surface by applying a curve fit to the set of tangent points.

19. The system of claim 1, wherein the first antenna and the second antenna are the same antenna and the first antenna is moved from the transmit location of the first antenna to a second location adjacent the transmit location of the first antenna.

20. A computer implemented method of improving an estimate of a two-dimensional cross section of a surface location, wherein the surface defines an interface between an object to image and an antenna, and further wherein the determination of the surface location is for use in an imaging system, the method comprising:

using a processor of a computer, estimating a first minimum propagation time for a first signal received at a first antenna, the first signal reflected from a surface;

using a processor of a computer, calculating a first distance between the surface and the first antenna using the estimated first minimum propagation time;

using a processor of a computer, defining a first circle centered at the first antenna, the first circle having a first radius equal to the calculated first distance;

using a processor of a computer, estimating a second minimum propagation time for a second signal received at a second antenna, the second signal reflected from the surface, and the second antenna adjacent a transmit location of the first antenna;

using a processor of a computer, calculating a second distance between the surface and the second antenna using the estimated second minimum propagation time;

using a processor of a computer, defining a second circle centered at the second antenna, the second circle having a second radius equal to the calculated second distance;

using a processor of a computer, defining a first tangent point, the first tangent point located on the second circle and on a line tangent to both the first circle and the second circle and in a direction of radiation of the first antenna toward the surface;

using a processor of a computer, estimating a third minimum propagation time for a third signal received at a third antenna, the third signal reflected from the surface, and the third antenna adjacent a transmit location of the second antenna;

using a processor of a computer, calculating a third distance between the surface and the third antenna using the estimated third minimum propagation time;

using a processor of a computer, defining a third circle centered at the third antenna, the third circle having a third radius equal to the calculated third distance;

using a processor of a computer, defining a second tangent point, the second tangent point located on the second circle and on a line tangent to both the third circle and the second circle and in the direction of the surface;

using a processor of a computer, defining a third tangent point that is the average of the defined first tangent point and the defined second tangent point; and using a processor of a computer, saving the defined third tangent point as an estimate of a location on the surface.

* * * * *

UNITED STATES PATENT AND TRADEMARK OFFICE
CERTIFICATE OF CORRECTION

PATENT NO. : 7,647,089 B2
APPLICATION NO. : 11/340214
DATED : January 12, 2010
INVENTOR(S) : Essex Julian Bond, Susan Carol Hagness and Barry Dean Van Veen It is certified that error appears in the above-identified patent and that said Letters Patent is hereby corrected as shown below:

Claim 18, Column 14, Line 53:

Replace "radium" with "radius"

Signed and Sealed this

Thirtieth Day of March, 2010

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,647,089 B2 |
| APPLICATION NO. | : 11/340214 |
| DATED | : January 12, 2010 |
| INVENTOR(S) | : Bond et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 971 days.

Signed and Sealed this

Sixteenth Day of November, 2010

David J. Kappos
*Director of the United States Patent and Trademark Office*